(12) United States Patent
McCormick

(10) Patent No.: US 7,521,021 B2
(45) Date of Patent: Apr. 21, 2009

(54) SYSTEM FOR IN SITU PROCESSING OF A TISSUE SPECIMEN

(75) Inventor: James B. McCormick, Lincolnwood, IL (US)

(73) Assignee: Leica Biosystems St. Louis LLC, St. Louis, MO (US)

(*) Notice: Subject to any disclaimer, the term of this patent is extended or adjusted under 35 U.S.C. 154(b) by 951 days.

(21) Appl. No.: 11/001,305

(22) Filed: Dec. 1, 2004

(65) Prior Publication Data

US 2005/0112034 A1 May 26, 2005

Related U.S. Application Data

(63) Continuation-in-part of application No. 10/723,692, filed on Nov. 26, 2003.

(51) Int. Cl.
*B01L 3/00* (2006.01)
(52) U.S. Cl. .................... 422/102; 422/63; 422/64; 422/67; 422/104; 206/473; 206/526
(58) Field of Classification Search ............. 422/63–67, 422/102, 104; 206/473, 526
See application file for complete search history.

(56) References Cited

U.S. PATENT DOCUMENTS

| | | | |
|---|---|---|---|
| 3,537,636 A | 11/1970 | Rochette | |
| 4,225,557 A | 9/1980 | Hartl et al. | |
| 4,420,353 A | 12/1983 | Levine | |
| 4,549,670 A | 10/1985 | Trendler | |
| 4,557,903 A | 12/1985 | McCormick | |
| 4,569,647 A | 2/1986 | McCormick | |
| 4,576,796 A | 3/1986 | McCormick | |
| 4,645,743 A | 2/1987 | Baker et al. | |
| 4,874,090 A | 10/1989 | Dyke | |
| 5,080,869 A | 1/1992 | McCormick | |
| 5,269,671 A | 12/1993 | McCormick | |
| 5,338,358 A | 8/1994 | Mizusawa et al. | |
| 5,662,639 A | 9/1997 | Tanaka et al. | |
| 5,665,398 A | 9/1997 | McCormick | |
| 5,817,032 A | 10/1998 | Williamson, IV et al. | |
| 5,928,934 A | 7/1999 | McCormick | |
| 6,060,039 A | 5/2000 | Roe et al. | |
| 2005/0112032 A1 | 5/2005 | McCormick | |
| 2005/0112034 A1 | 5/2005 | McCormick | |

FOREIGN PATENT DOCUMENTS

| | | |
|---|---|---|
| EP | 0245969 A | 11/1987 |
| EP | 0807807 A | 11/1997 |
| EP | 1 321 757 A1 | 6/2003 |
| EP | 1321757 A | 6/2003 |

OTHER PUBLICATIONS

Int'l Search Report for PCT/US2005/042933, not yet published, McCormick.

*Primary Examiner*—Jill Warden
*Assistant Examiner*—Jyoti Nagpaul
(74) *Attorney, Agent, or Firm*—Thompson Coburn LLP; Kevin M. Kercher, Esq.

(57) ABSTRACT

The present invention is directed to a system for use in the preparation in situ of tissue specimens for histological examination. The system includes a cassette, a specimen mounting card and a base mold. The invention also is directed to a method of processing a tissue sample for histological examination which does not require re-orienting the selected cutting plane in the specimen transfer step. Instead, the tissue sample remains oriented in a desired position throughout processing.

8 Claims, 7 Drawing Sheets

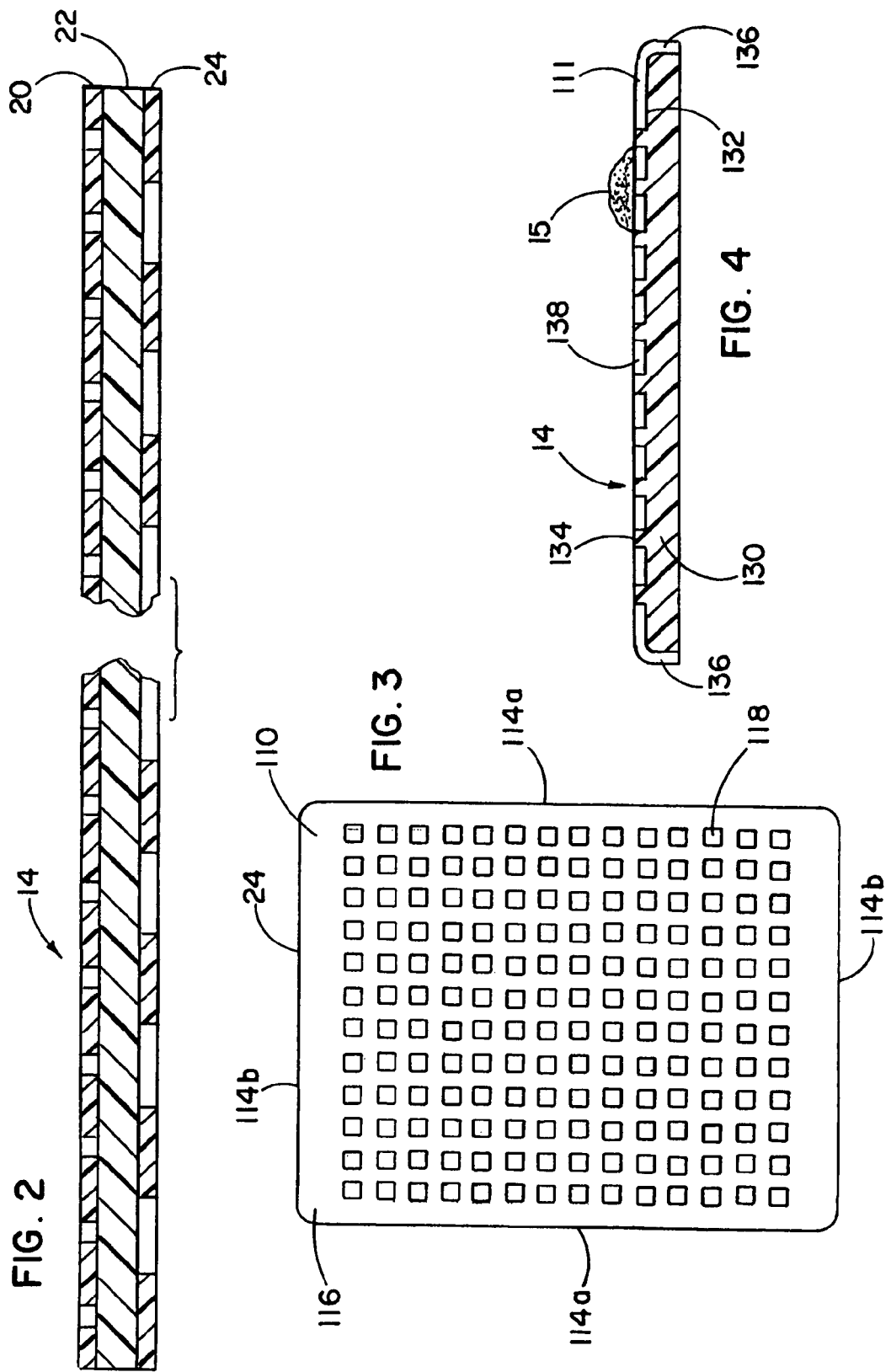

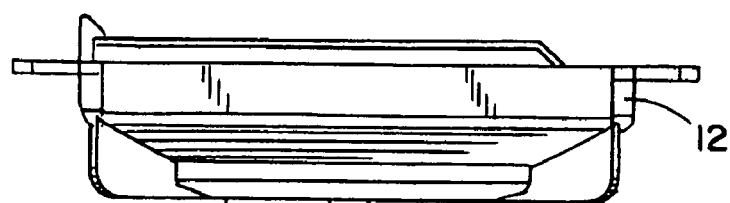
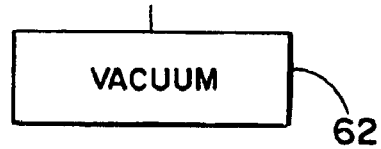
FIG. 8
FIG. 9
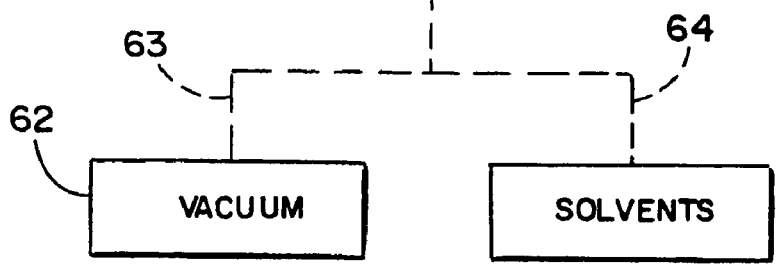
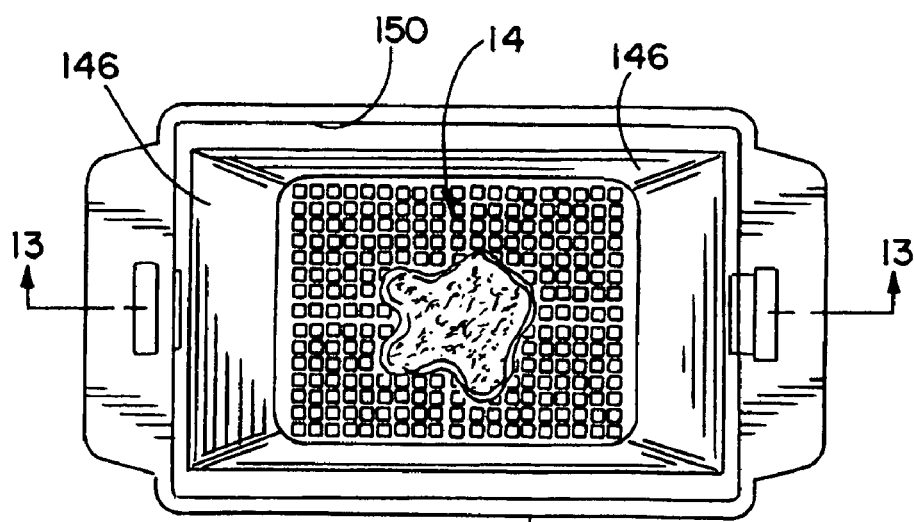
FIG. 12

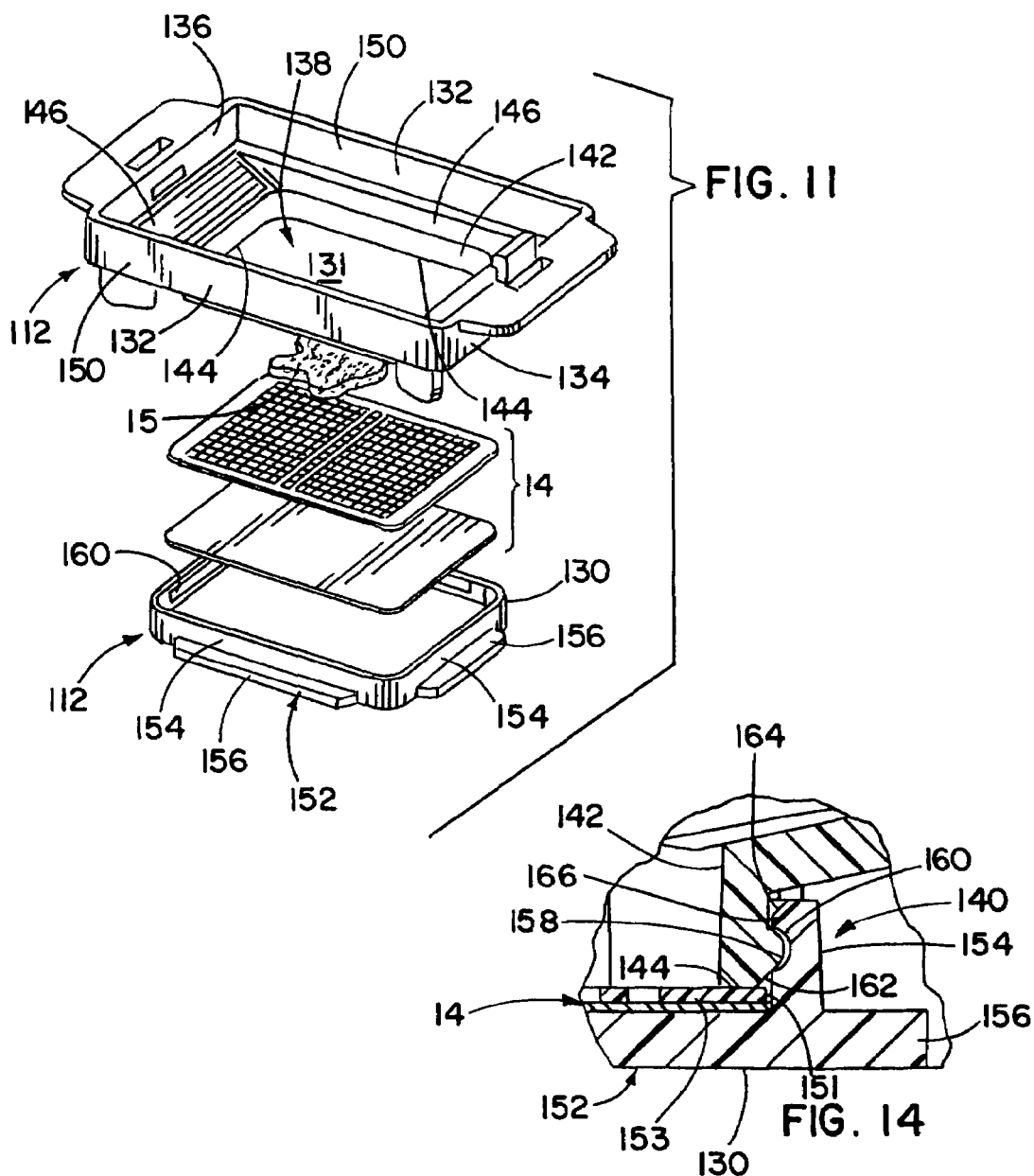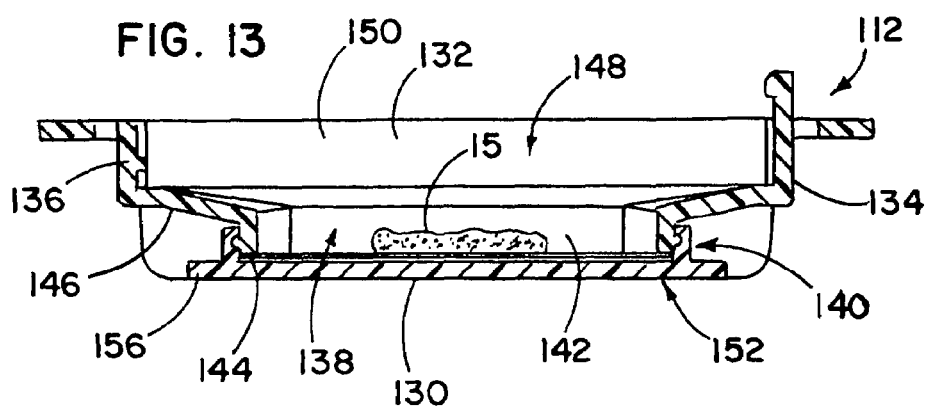

SYSTEM FOR IN SITU PROCESSING OF A TISSUE SPECIMEN

CROSS-REFERENCE TO RELATED APPLICATION

This application is a continuation-in-part of prior application Ser. No. 10/723,692, filed Nov. 26, 2003, which is hereby incorporated herein by reference in its entirety.

FIELD OF THE INVENTION

The present invention relates to an apparatus and method for preparing a tissue specimen for histological examination and, more particularly, to an apparatus and method for processing the tissue specimen from the time of collection of the specimen to the preparation of the microscope slide.

BACKGROUND OF THE INVENTION

It is a standard procedure to prepare tissue samples for microscopic examination by embedding the tissue in paraffin and slicing the paraffin-embedded tissue very thinly with a microtome. Preparatory to embedding, the tissue is treated in various solutions appropriate to its examination and long-term stability. Typically, prior to paraffin embedding, the tissue sample is fixed, dehydrated, and cleared and then infiltrated with molten paraffin.

Typically, the tissue sample collected for examination is a unitary, connected portion of tissue, however, small parts of the tissue sample may be dislocated during tissue processing. Alternatively, a biopsy may be performed on minute fragments less than 1.0 mm in diameter, such as bronchial washings, cytology preparations and aspiration biopsies which may be gathered by skinny needles or imaging technology-guided tissue biopsy devises. Generally, this technique is called "tissue processing," and it includes the following: (1) collection of the specimen; (2) fixation of the specimen to preserve tissue components; (3) sampling of a representative portion or aliquot; and (4) cutting of the non-processed tissue in a section plane to be presented to the microtome blade (for microscopic examination and information collection) and placement of this plane face down in a tissue processing cassette for containment during the "tissue processing phase."

Information obtained in the microscopic study of biological tissue is taken from microtome cut sections that, on average, are less than 10 µ thick. Thus, in view of the small size of the tissue sample and the precision with which the microtome cut sections are cut, it is of paramount importance to select a cutting plane and to maintain this plane as closely as possible, if not exactly, during processing, embedding and sectioning. Further, in the instance of minute specimens (approximately 1 mm or less), it may also be desirable to preserve the orientation of the tissue sample in relation to the adjacent structures from which it was collected. Such information may provide guidance for surgical or other treatments.

Tissue placed in a processing cassette may be fresh or fixed. The tissue sample is then passed through fixatives to remove water from the sample. Following dehydration, the tissue sample is then processed with a solvent that will dissolve fatty materials and "clear" the tissue sample. After being "cleared", the tissue sample is placed in molten paraffin and it is infiltrated with the wax. Molten wax replaces the solvent which will evaporate or be diluted to trace levels, causing all the tissue to be infiltrated with a common wax binder.

Next, the cassette is opened and the infiltrated tissue is placed into a metal or similar base mold filled with melted wax. A considerable effort must be made at this moment to cause the "face down" selected cutting plane of the tissue to be positioned in the exact same planar relationship that was selected by the doctor or technician who placed the sample and selected the portion of the tissue that would be cut in microtomy. It is critical in many examinations, such as cancer diagnosis, to maintain the parallel relationships of: (a) selected cutting surface; (b) microtomy cut surface; (c) glass slide stained and covered cut section; and (d) microscopic section orientation for examination.

The technician thus must attempt to present the specimen to the microtome cutting blade in the exact position previously selected. The technician prepares the specimen for microscopic examination by subsequently mounting, staining and cover-slipping the microtome cut section on a microscope slide. Although it is desirable to maintain the positioning of the specimen, it is very difficult to control the position of the specimen particularly with minute tissue samples. A small (0.25-1.0 mm) specimen may likely shift its position in the cassette during processing or when it is removed from the processing cassette to the embedding mold prior to wax casting, so that the pre-selected position of the specimen may be lost.

Apparatuses are known that may be used for processing of tissue samples, such as described in U.S. Pat. Nos. 4,557,903 and 4,569,647, both to McCormick. In both the '903 and '647 patents, the tissue sample is deposited somewhat randomly in the cassette. It is a limitation that, although the tissue sample is disposed in an enclosed area, it may move freely within that area as the tissue sample is contacted with solvents during processing. Additionally, the apparatus of the '903 patent requires removing the tissue sample from the cassette and placing it in a mold for casting in paraffin. A shortcoming of the '903 and '647 patents is their inability to maintain the tissue sample in a desired orientation throughout processing.

There remains a need for an apparatus and processing method that permits the tissue plane selected by the surgeon or pathologist to be processed in situ without disturbing the orientation of the tissue specimen. More particularly, there is a need for an assembly and method that maintains the desired position of the tissue sample during the fixing, processing, and wax embedding steps, as well as during subsequent sectioning in a microtome and mounting of the desired section on a glass slide for staining, cover-slipping and microscopic examination. Such a system should be adaptable for both large specimen sections and minute fragments of less than 1 mm in size.

SUMMARY OF THE INVENTION

The present invention is directed to a system and method for use in the preparation in situ of a tissue specimen for histological examination. The system and method allows a selected cutting plane of the specimen to be maintained throughout processing, from the time the plane is selected through sectioning of the specimen in the microtome to improve the accuracy and effectiveness of histological examination. The system includes a card or positioning member for mounting the tissue specimen in the desired position that is maintained throughout processing, a cassette or carrier member for receiving the card with the mounted tissue specimen and for subsequently mounting the processed tissue specimen in a microtome, and a base mold having a lower recessed chamber for receiving the card with mounted tissue specimen.

The mounting card may include an essentially non-adhesive surface, such as metal or polyester, and a porous, absorbent underlayment material. The upper surface of the mounting card may include a thin film, such as polypropylene, polytetrafluoroethylene, polyethylene, polyester and nylon films. Alternatively, the upper surface may include a thin (about 0.004 to 0.006 inch thick) piece of metal, such as stainless steel, or plastic. The upper surface may be perforated to have a void space sufficient to allow the denatured tissue juice to pass therethrough so as to form a protein bridge into the absorbent underlayment material. Or, in the instance of previously fixed tissue, the penetration and encapsulation by a molten agar or gel that when cool will process and embed for microtome sectioning.

The base mold may include an upper interior area for receiving the cassette and a lower chamber for receiving the mounting card with specimen. The front and back walls may have lines of weakness to allow the walls to be separated from the base mold to facilitate access to the interior of the base mold when it is desired to remove the casting block. The base mold also may include an opening in the lower chamber so that a process line may be connected to the base mold. The base mold may also include a removable bottom wall.

In accordance with the method of the invention a tissue specimen is collected and a desired cutting plane identified. The specimen is disposed on the surface of a semi-rigid or rigid mounting card with the desired cutting plane positioned downwardly on the surface of the card. A carbohydrate or protein-based glue or the like may be utilized in mounting the specimen on the card. As an example, such glue may be a polysaccharide, including 5% agar agar or polyamide gel. The card with applied specimen may be placed in a cassette for transporting the specimen. The specimen so mounted on a card within a cassette may be placed in an appropriate container of tissue fixative for transport to the processing laboratory. Alternatively, the specimen on the mounting case may be covered with a fixative gel, such as 10% formalin in a resin gel base. The specimen next may be processed with suitable fluids necessary for preparing the specimen for histological examination. The specimen on the card may be processed in the cassette or may be removed from the cassette and placed in a base mold for processing.

Subsequent to processing, the specimen card is placed in the base mold, if processing did not occur in the base mold, for embedding. The card with the specimen may be placed in a lower chamber of a base mold, while the cassette may be placed in an upper chamber of the base mold above the card. Embedding material, such as paraffin is introduced into the base mold. Before the introduction of the embedding material, a vacuum may be drawn to flatten the card against the base mold to provide a smooth planar surface. Or, as an alternative method, the lower chamber of the mold may be open and a closure containing the specimen card applied to the opening thus positioning the card, specimen face up, in the bottom chamber for wax casting.

The embedded specimen and cassette may be recovered from the base mold in the form of an investment casting tissue block which includes the cassette as the base of the block and an outwardly extending, specimen-containing examination portion of the block. The block may be mounted in a parallel relationship to the microtome by engaging the cassette with the microtome chuck, and the block may be sectioned by the microtome blade as a planar section.

BRIEF DESCRIPTION OF THE DRAWINGS

FIG. 2 is an enlarged cross-sectional view generally taken along line 2-2 of FIG. 1;

FIG. 3 is a top plan view of an exemplary backing member for the positioning member of FIG. 1;

FIG. 4 is a cross-sectional view of a positioning member in accordance with an alternative embodiment of the present invention;

FIG. 8 is a side elevational view of the assembly of FIG. 5 and a schematic showing a vacuum attachment through the bottom wall of the base mold;

FIG. 9 is a side elevational view of the assembly of FIG. 5 and a schematic showing a vacuum attachment and fluid port attachment through the bottom wall of the base mold;

FIG. 11 is an exploded perspective view of an alternative base mold embodying features of the present invention illustrating an exemplary positioning member and tissue sample;

FIG. 12 is a top plan view of the base mold of FIG. 11 illustrating an exemplary tissue sample disposed on the positioning member;

FIG. 13 is a cross-sectional view of the base mold of FIG. 12 taken generally along line 13-13 illustrating an exemplary positioning member and tissue sample within the base mold;

FIG. 14 is an enlarged, detail view of a portion of the base mold of FIG. 13;

DETAILED DESCRIPTION OF THE FIRST EMBODIMENT

Figure 1:
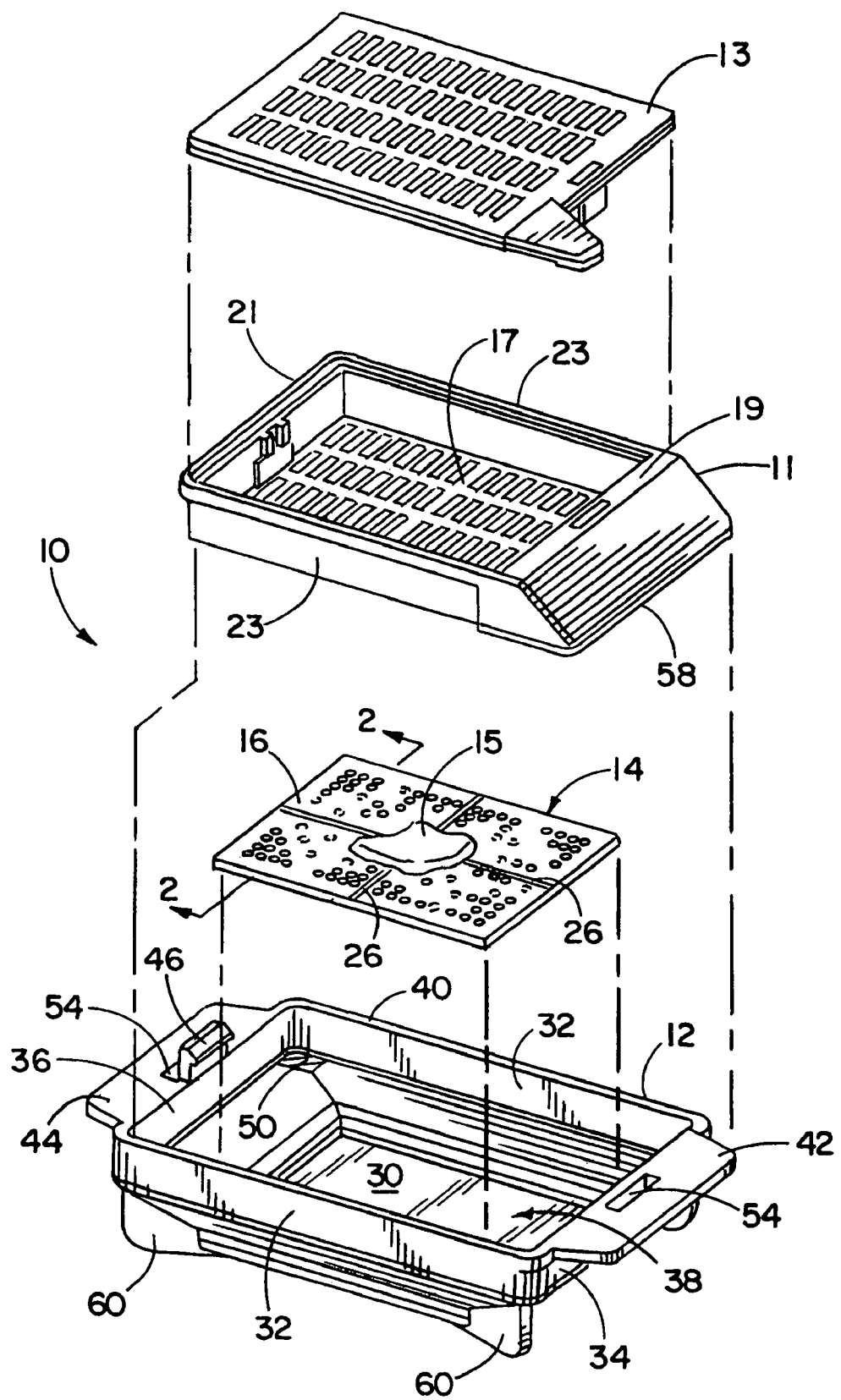
FIG. 1 is an exploded perspective view of an assembly for in situ processing of a tissue sample embodying features of the present invention illustrating an exemplary carrier, positioning member, base member, and tissue sample.

Referring to FIG. 1, there is illustrated an assembly for in situ processing of a tissue sample embodying features of the present invention. The preferred assembly 10 generally includes a cassette or carrier member 11 with lid 13, a specimen mounting card or positioning member 14, and a base mold 12. The assembly 10 allows a tissue sample 15 to be initially oriented in a desired position on the specimen mounting card 14 prior to processing which is maintained throughout subsequent processing of the tissue sample 15 and casting in paraffin, or wax. In this aspect, the specimen mounting card 14 having the tissue sample 15 positioned thereon may be first deposited in the cassette 11 for processing and then deposited in the base mold 12 to be cast in a wax block, with the cassette 11 serving as the base of the block opposite the tissue sample 15. Tissue processing and casting of the tissue sample 15 on the specimen mounting card 14 also may be accomplished within the base mold 12, and in the alternate method in the snap on holder beneath the center of the open bottom base mold.

The cassette 11 of the assembly 10 may be any cassette for preparing tissue samples for histological examination known in the art that provides an enclosed area for containing a tissue sample during transport and processing. Preferably, the cassette should be sized to cooperate with the base mold 12. Exemplary cassettes are as described in U.S. Pat. Nos. 5,665,398 or 5,928,934, both to McCormick, which are hereby incorporated herein by reference in their entirety; although, it will be recognized that other types of cassettes could also be effectively utilized. The cassette 11 generally includes a bottom wall 17, a front wall 19, a back wall 21 and two side walls 23.

The specimen mounting card 14 comprises a semi-rigid or rigid, generally planar card member. The mounting card 14 is a generally thin, rectangular-shaped card member, with dimensions sized to engageably fit within the cassette 11. The specimen mounting card 14 also may be square-shaped or otherwise configured to generally conform to the shape and dimensions of the cassette 11. If desired, the top surface 16 of the mounting card 14 may be provided with target lines 26 and/or millimeter (or other dimensional) scale markings to provide a measurement scale for identification and sizing of a sample.

As illustrated in FIG. 2, the mounting card 14 comprises at least one layer and preferably two or more layers. The first layer 20 includes a thin film, such as polypropylene, polytetrafluoroethylene, polyethylene, polyesters and nylon. As an example, the first layer 20 may be Mylar® polyester film by DuPont. The first layer 20 provides a relatively smooth, non-adhesive surface so that the tissue sample 15 does not adhere to the mounting card 14 to such a degree that it is difficult to remove the wax cast tissue sample 15 in the casting step. Additionally, the top layer 20 is selected so that paraffin generally will not adhere to it in order to facilitate separation of the solidified wax block cast from the mounting card 14 in the casting step.

Preferably, the film of the first layer 20 is perforated and has a porosity of at least about 15% and no more than about 70% total void space, and more preferably at least about 50% and no more than about 60% total void space. A relatively high porosity is desired to allow the denatured tissue juice (serum) or protein glue to pass through the film to the layer or layers below, as well as to allow the tissue processing solvents to pass through the mounting card 14 during processing.

A second layer 22 generally is an absorbent, porous paper. Preferably, the second layer 22 includes an absorbent cellulose paper, such as a filter paper. The second layer 22 preferably has a filter passage of approximately 40 to 80% and, more preferably, approximately 60 to 70%, to allow tissue serum, as well as tissue processing solvents, to readily pass through the layer and the specimen mounting card 14.

Generally, the second layer 22 provides the structure to which the tissue sample 15 bonds to the specimen mounting card 14. The tissue sample 15 is mounted on the card 14 as a result of a protein bridge that forms between the denatured tissue juice, when the tissue is in the fresh state, and the fibers of the paper in the second layer 22. Alternatively, the tissue sample may be mounted to the card 14 as a result of a protein bridge that forms between a protein glue and the fibers.

To impart increased rigidity to the specimen mounting card 14, the specimen mounting card 14 may comprise a third layer or backing member 24. The third layer preferably comprises a rigid or semi-rigid material and engageably contacts the second layer 22 at the surface opposite the first layer 20.

As an example, the third layer 24, may be an acetyl molded backing or a metal backing and may be provided with perforations or other apertures to allow flow of fluids therethrough. Alternatively, the mounting card 14 may be disposed within a frame of sufficient rigidity that extends around the perimeter of the specimen mounting card 14 to hold the layers 20, 22 together and to provide overall rigidity to the specimen mounting card 14.

As illustrated in FIG. 3, the third layer 24 may comprise a planar metal plate member 110. Preferably, the plate member comprises two opposing longer side edges 114*a* and two shorter opposing side edges 114*b* extending between the longer side edges 112 to define a generally planar, rectangular surface 116. The surface 116 is provided with a plurality of apertures 118 to allow fluids to pass through the plate member 110. The apertures 118 are positioned across the surface 116 to create a predetermined void space in the surface 116. Preferably, the plate member 110 has a void space of at least about 60% and no more than about 85% and, more preferably, at least about 70% and no more than about 80%. The apertures 118 may be of any suitable dimension and number, and may be arranged in any pattern sufficient to achieve the predetermined void space. The plate member 110 imparts a predetermined degree of rigidity to the mounting card 14 when it is desired to use a frame, adhesive or other apparatus to maintain the various layers of the specimen mounting card 14 adjacent one another.

Alternatively, the plate member 110 may be provided with a plurality of tabs, extensions, or bars around its outer perimeter (not shown). The tabs facilitate the assembly of the mounting card 14 without adhesive or a frame. For example, the layers of the mounting card are positioned at the top surface of the plate member 110. The tabs are then bent upwardly around the outer perimeter of the other layers and the ends are pressed downwardly onto the layers to maintain the layers in engageable contact with one another and with the plate member 110.

In another embodiment, as illustrated in FIG. 4, the specimen mounting card 14 comprises a plate member 111 having a paper layer 130 positioned against the back surface 132 of the plate member 111, with the paper 130 filling the openings 134 of the plate member 111. The paper layer 130 may comprise paper pulp slurry which is aspirated, or otherwise applied, onto the back surface 132 of the plate member 111 and into the openings 134. The paper layer 130 also may comprise heavy filter paper, or the like, that is pressed into the back surface 132 and into the openings 134. The plate member 111 is constructed of a material selected to provide, in addition to a sufficiently rigid structure, an essentially non-stick surface to which paraffin or other casting material will not adhere. To impart these characteristics, the plate member 111 may be constructed of a non-reactive metal or alloy, such as stainless steel and the like, or plastic, such as polypropylene, polyethylene and the like. The plate member 111 may be provided with a skirt 136 that extends downwardly around the outer perimeter to provide a cavity into which the paper layer 130 may be disposed. The plate member 111 also may include tabs or the like (not shown) for securing the paper layer 130 to the back surface 132 of the plate member 111. Alternately the metal plate material may be coated on one side with a low melt polyethylene and, after a punch perforation, a hot roller application will weld the backing paper substrate to create a lamination of metal-polyethylene film and paper. The adhesion of lamination to paper would be the closed space of the metal surface.

In this embodiment, the combination of plate member 111 and paper layer 130 provide a specimen mounting card 14 onto which the tissue sample 15 may be removably mounted for processing. The plate member 111 preferably has a void space of at least about 40 and no more than about 80%, more preferably, at least about 70 and no more than about 85%, and most preferably about 65%. The paper layer 130 fills the openings 134 and extends approximately to the upper surface 138 of the plate member 111.

The portions of the paper layer 130 exposed through the openings 134 generally provide the structure to which the tissue sample 15, which is deposited on the upper surface 138 of the plate member 111, bonds, i.e., the denatured tissue juice from the tissue sample 15 forms a protein bridge with the paper layer 130 through the openings 134. When it is desired to remove the tissue sample 15 from the mounting card 14 after the tissue sample 15 has been cast in paraffin block, the plate member 111 facilitates separation of the cooled paraffin block from the specimen mounting card 14, because the cooled paraffin generally will not adhere to the plate member 111.

In another embodiment, which is particularly suitable for small specimens (approximately 1 mm thick), the specimen mounting card 14 is a perforated, silicone-treated stiff paper or metal with a thickness of about 0.03 mm. The denatured tissue juice, along with the mountant warm protein or polysaccharide glue, if used, will bond the tissue sample to the mounting card by gripping the adjacent holes of the perforated paper.

Although the mounting card 14 has been described as having two or more layers of differing materials, it should be understood that the mounting card 14 may comprise any number and/or combination of layers. For example, in another embodiment, the mounting card 14 may comprise only the first layer 20 and the second layer 22, with an adhesive, such as acrylic glue, epoxy adhesive, or the like, applied around the perimeter of the mounting card 14 in an amount sufficient to maintain the two layers 20, 22 in contact with one another, as well as to provide a predetermined degree of rigidity. Alternatively, the mounting card 14 may be laminated with the adhesive.

Referring back to FIG. 1, the base mold 12 is generally rectangular in construction and is open to the interior surface at the top. The base mold 12 comprises a bottom wall 30, stepped side walls 32, a stepped front wall 34, and a stepped back wall 36. The base mold 12 is constructed of a lightweight, rigid material. For example, the base mold 12 may be constructed of a relatively inexpensive material, such as polypropylene, polyethylene, and the like, if the base mold 12 is intended for single use applications. The base mold 12 also may be constructed of a more durable material, such as a non-reactive metal or alloy, including stainless steel and the like. With more durable material, the base mold may be used more than once or connected to an in-line process, which is described below.

Figure 6:
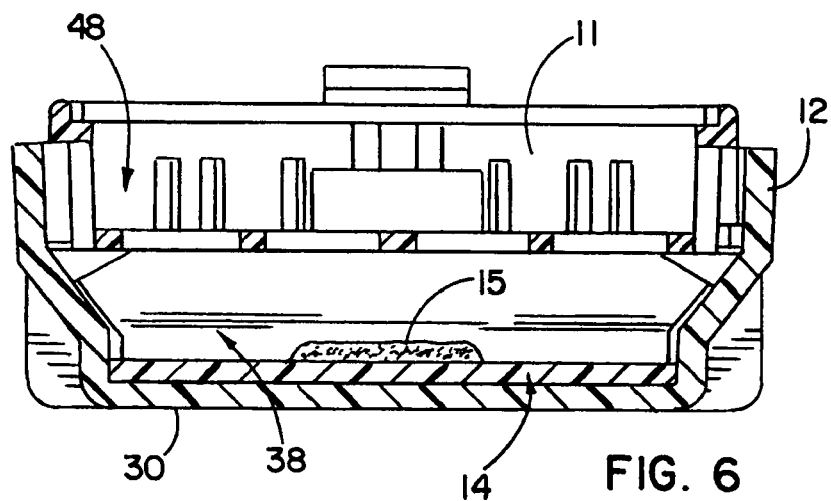
FIG. 6 is a cross-sectional view generally taken along line 6-6 of FIG. 5.

The walls 32, 34, 36 each extend upright from the bottom wall 30 a desired height to define a lower recessed chamber 38 at the interior of the base mold 12. Preferably, the dimensions of the bottom wall 30 are just larger than those of the mounting card 14 so that space between the card 14 and the walls 32, 34, 36 is limited but allows the card 14 to be readily disposed within the lower chamber 38. The depth of the lower chamber 38 is at least as high as the thickness of the mounting card 14, to allow the mounting card 14 to be disposed entirely within the chamber 38, as best shown in FIG. 6. The walls 32, 34, 36 at the lower chamber 38 may be undercut to better hold the mounting card 14 in the desired planar position within the lower chamber 38, as well as to retain the mounting card 14 when it is desired to separate the wax block with tissue sample 15 embedded therein from the mounting card 14.

From the lower chamber 38, the walls 32, 34, 36 angle outwardly and upwardly, thereby providing increased cross-sectional area in the interior of the base mold 12. Generally, the side walls 32 project upwardly at an angle steeper than the angle at which the front and back walls 34, 36 extend. Above the angled portions, each of the walls 32, 34, 36 extend upright to the upper perimeter 40 of the base mold 12 to define an upper receiving area 48.

Figure 5:
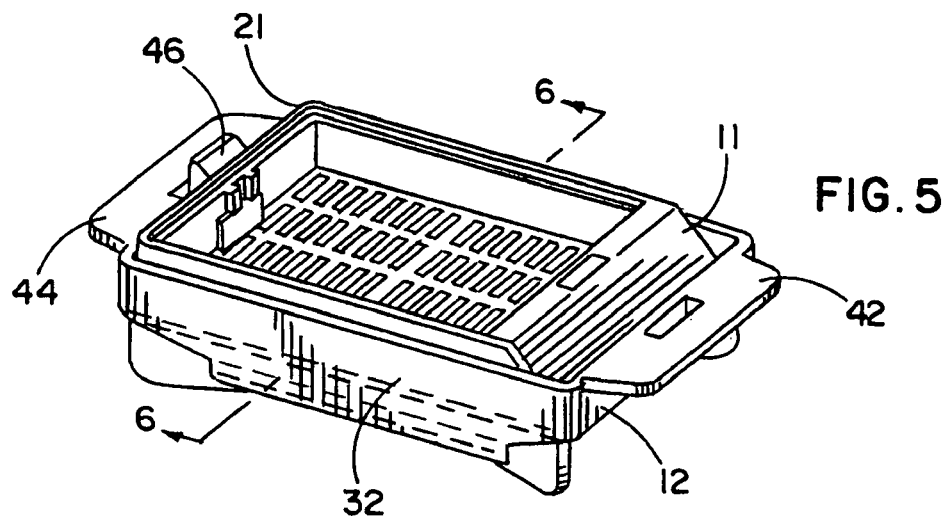
FIG. 5 is a perspective view of the assembly of FIG. 1, showing the carrier engageably mounted on the base mold.
Figure 7:
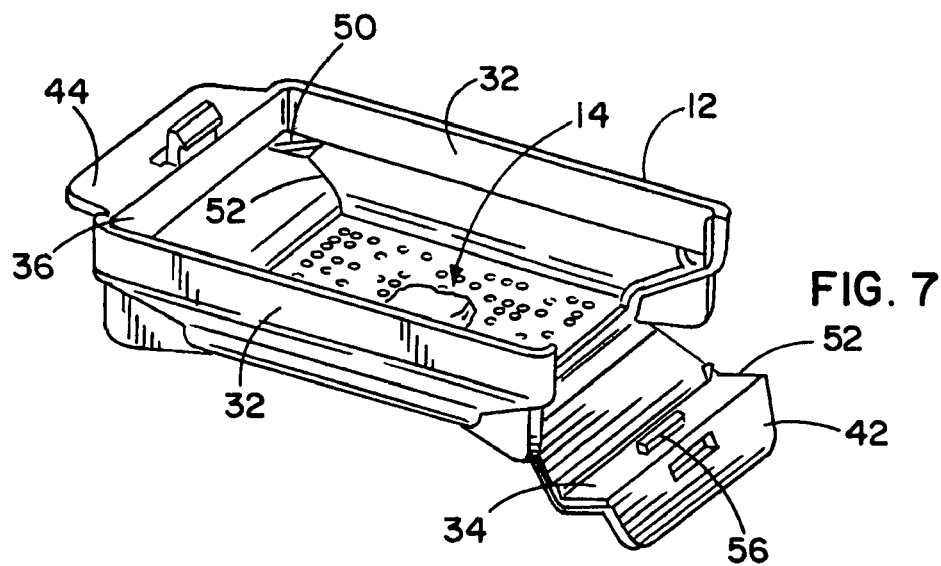
FIG. 7 is a perspective view of the base mold of FIG. 1 having the positioning member disposed therein, showing a front wall of the base mold in an open position.
Figure 10:
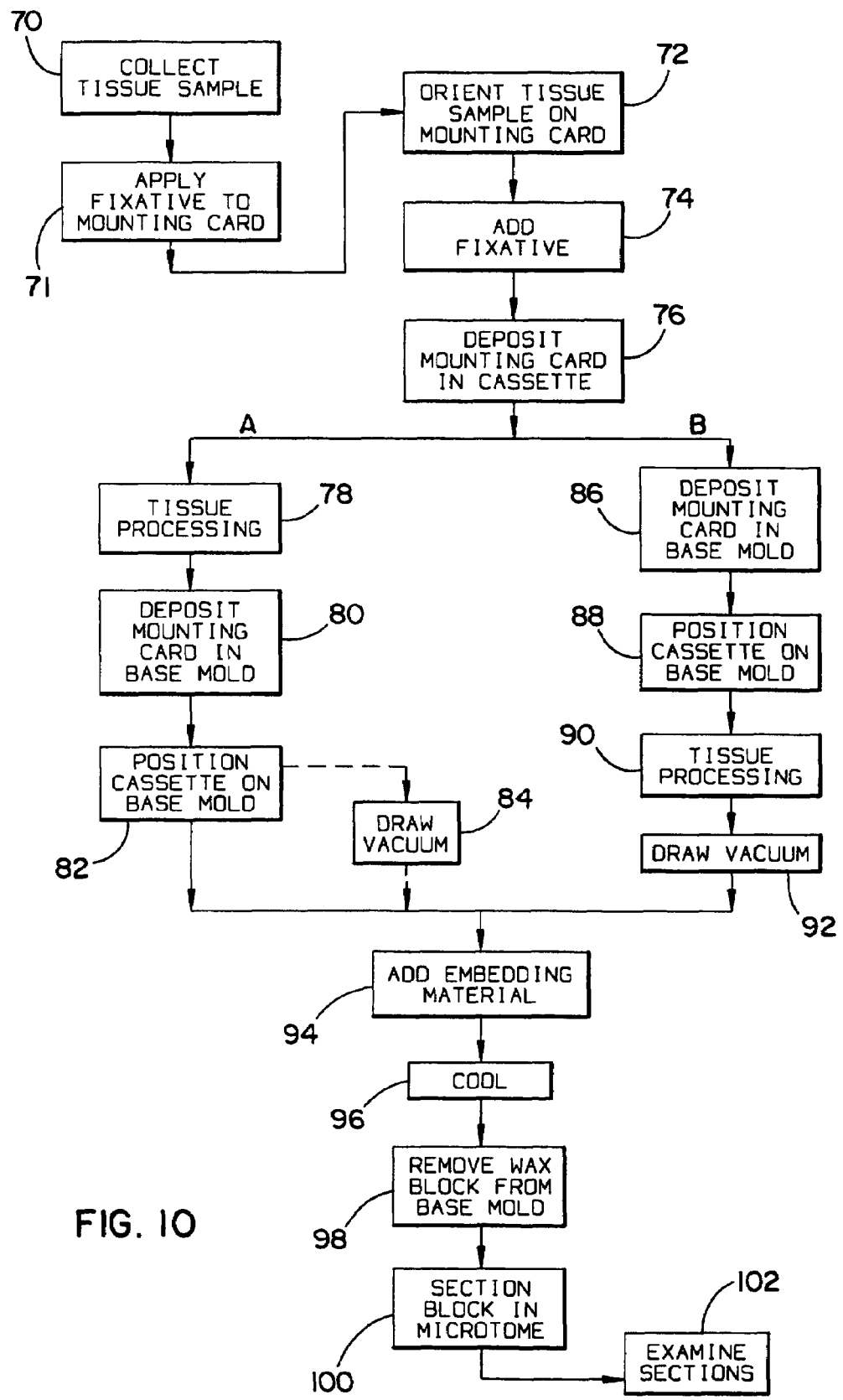
FIG. 10 is a process flow diagram of the method of the present invention.

Referring to FIGS. 5-7, the upper receiving area 48 preferably has a cross-sectional area just large enough to receive the cassette 11. Stacking lugs 50 may be provided at the four interior corners where the uppermost upright sections of the walls 32, 34, 36 intersect the angled sections of the walls 32, 34, 36. Alternatively, a bar or other projection (not shown) may be provided for support at the side walls and/or front and back walls for stacking two or more base molds or a cassette within a base mold.

A first tab 42 extends generally horizontally from the perimeter 40 at the front wall 34. A similar second tab 44 extends from the back wall 36. Both tabs 42, 44 extend along substantially the width of the front and back walls 34, 36. The second tab 44 is provided with a finger member 46 that projects upwardly from the tab 44.

When the cassette 11 is disposed in the base mold 12 at the upper receiving area 48 (FIG. 5), the finger member 46 engages the back wall 21 of the cassette 11 to removably secure the cassette 11. A rib 56 (FIG. 7) on the interior surface of the front wall 34 is positioned so as to cooperate with the tab 44 in securing the cassette 11 as described in U.S. Pat. No. 5,269,671, issued to McCormick, which is incorporated herein by reference. When the cassette 11 is disposed in the base mold 12, the lower edge 58 of the front wall 19 snaps into place below the rib 56. The stacking lugs 50 provide additional support for the cassette 11 when it is disposed in the receiving area 48.

The front and back walls 34, 36 may be provided with weakened lines 52 that extend between the lower chamber 38 and the upper perimeter 40 adjacent the edges along which the walls 34, 36 intersect the side walls 32. The weakened lines 52 facilitate separation of the front and back walls 34, 36 so that the walls may be pulled outwardly and downwardly away from the base mold 12 (FIG. 7). Deflecting back the walls 34, 36 in this manner provides increased access to the interior of the base mold 12 to facilitate removal of the wax block. An implement may be inserted into openings 54 in the tabs 42, 44 and used as a lever to break the walls at the weakened lines 52 and pull back the front and back walls 34, 36.

Preferably, the weakened lines 52 do not extend down into the lower chamber 38. By maintaining the integrity of the walls 32, 34, 36 at the lower chamber 38, the mounting card 14 will be better retained within the chamber 38 when it is desired to separate the casting from the mounting card 14 and remove the casting from the base mold 12 for further processing.

The base mold 12 also preferably comprises outwardly extending feet 60. The feet 60 extend from the walls 32, 34, 36, preferably at the corners. The feet 60 are positioned and configured to provide sufficient support and stability for the base mold 12.

In another embodiment of the present invention, the base mold 12 is configured to allow a vacuum 62 to be drawn from below the bottom wall 30, as illustrated in FIG. 8. The bottom wall 30 of the base mold 12 may include perforations or similar openings 61 of sufficient size and spacing to allow the desired vacuum to be drawn. The vacuum pulls the mounting card 14 downwardly against the bottom wall 30 to provide a planar orientation. By drawing a vacuum 62 from below the bottom wall 30 as the molten paraffin is poured into the base mold 14, the top layer 20 of the mounting card 14 will be pulled taut and flat against the bottom wall 30. With the vacuum being drawn, the wax block casting will be formed on a generally planar surface so as to have few or no imperfections that will result in small pieces of tissue and wax being sliced separately from the casting.

In another embodiment of the present invention, as illustrated in FIG. 9, the base mold 12 may be utilized in an in-line process. A process line 64 is connected to the bottom wall 30 of the base mold 12 for introduction of solvents into the base mold 12 and subsequent extraction of the solvents. In this embodiment, the solvents for processing the tissue sample 15 are mechanically introduced into the base mold 12 via the process line 64 instead of being manually introduced from the top. After processing is completed, the solvents are removed from the base mold 12 via the process line 63, which is also connected to the bottom wall 30. In this aspect, the processing of the tissue sample 15 may occur via drip extraction. The vacuum 62 may also be connected to process line 63 for use either during removal of the process solvents or for pulling the top layer 20 of the mounting card 14 as described above. Thus, the base mold 12 may also be an essentially self-contained processing unit.

Referring to FIGS. 11-16, alternative base mold 112 is illustrated. The base mold 112 is similar to base mold 12 with the differences highlighted below. In general, the base mold 112 includes stepped side walls 132, a stepped front wall 134, a stepped back wall 136, and a removable bottom wall 130 having a snap-fit connection 140 with at least one of the walls 132, 134, and 136. Portions of the walls 132, 134, and 136 generally form a lower recessed chamber 138 and an upper receiving area 148. The walls 132, 134, and 136 have bottom edges 144 that generally define a tissue receiving opening 131.

When using the base mold 112, handling of the positioning member 14 is minimized. For instance, the positioning member 14 may be placed on the removed bottom wall 130, which is then connected to the lower recessed chamber 138 through the snap-fit connection 140. In this manner, the positioning member 14 with the deposited tissue sample 15 thereon is directly inserted into the lower recessed chamber 138 through the tissue receiving opening 131 rather than the user guiding the positioning member 14 through the upper receiving area 148 or around walls 132, 134, and 136.

Figure 15:
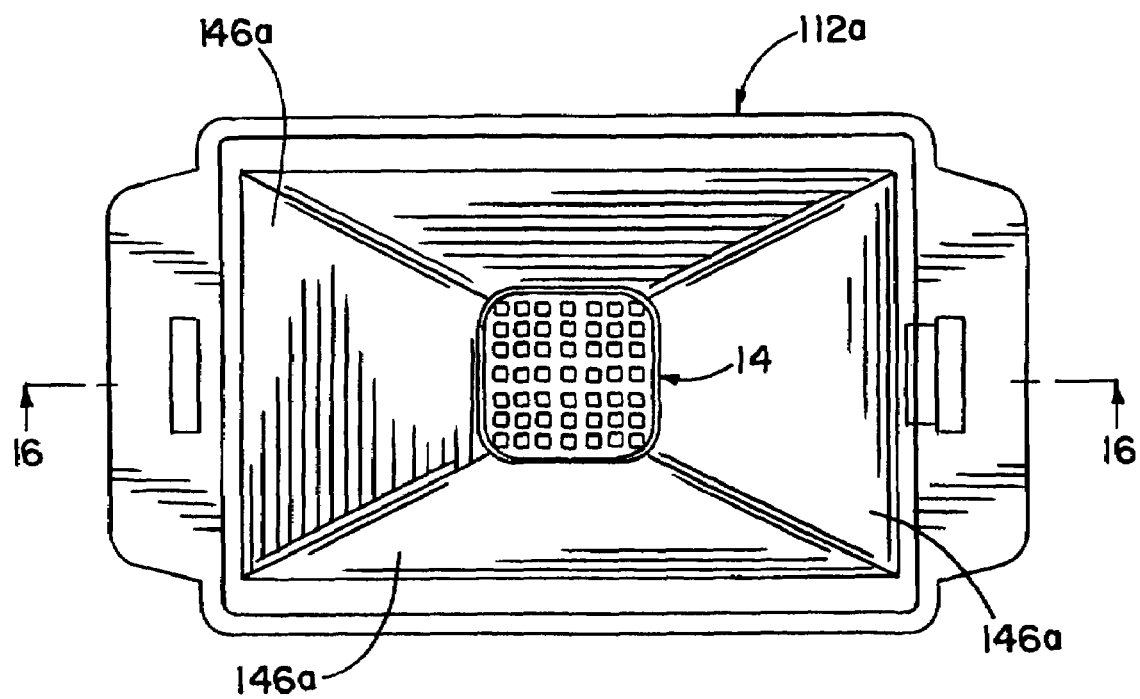
FIG. 15 is a top plan view of an alternative base mold shown with an exemplary positioning member.
Figure 16:
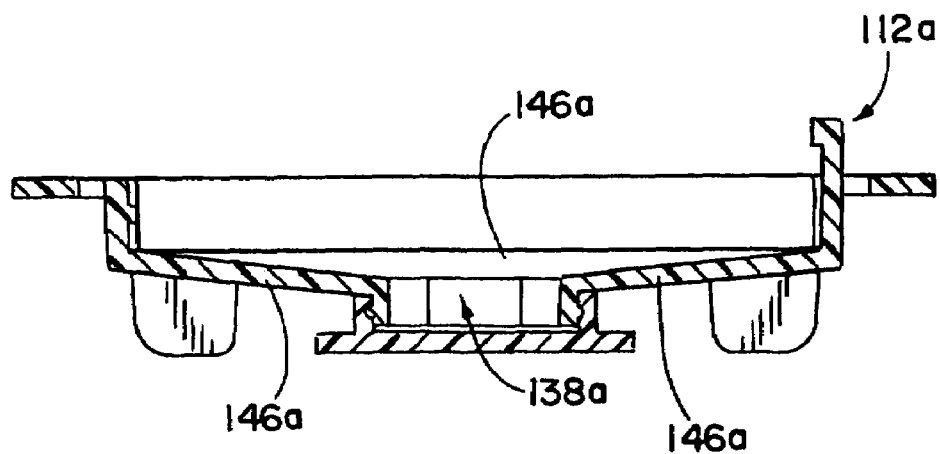
FIG. 16 is a cross-sectional view of the base mold of FIG. 15 taken generally along line 16-16.

More specifically, as illustrated in FIGS. 11-14, the lower recessed chamber 138 is formed by portions of walls 132, 134, and 136. For instance, the lower recessed chamber 138 is generally defined by lower wall portions 142, which are the lowermost step portions of the walls 132, 134, and 136. Each lower wall portion 142 terminates in the bottom edges 144. The size of the lower recessed chamber 138 is determined by intermediate wall portions 146, which are the inner step portions of the walls 132, 134, and 136. The intermediate wall portions 146 preferably angle upwardly away from lower wall portions 142. Each intermediate wall portion has a width that generally determines the size of the lower recessed chamber 138 and, thus, the tissue receiving opening 131. For example, FIGS. 12 and 13 illustrate the base mold 112 with the intermediate wall portions 146 having generally narrower widths to define a larger, lower recessed chamber 138. Alternatively, as illustrated in FIGS. 15 and 16, the base mold 112*a* may have generally longer, intermediate wall portions 146*a* to define a generally smaller lower recessed chamber 138*a*.

The upper receiving area 148 is generally superimposed above the lower recessed area 138. As with the lower area 138, the upper receiving area 148 is also defined by portions of the walls 132, 134, and 136. In this instance, upper wall portions 150 form the upper receiving area 148. The upper wall portions 150 are the uppermost steps of the walls 132, 134, and 136 and generally extend upwardly away from the intermediate wall portions 146, preferably in a generally vertical orientation. While not illustrated in FIGS. 11-16, the upper receiving area 148 is sized to receive the cassette or carrier 11 similar to base mold 12.

Bottom wall 130 preferably defines a cartridge or module 152 sized for receiving the positioning member 14. Cartridge 152 preferably includes side walls 154 that extend upwardly away from bottom wall 130. Preferably, the dimensions of the cartridge 152 are just larger than those of the positioning member 14 so that a space 151 between the positioning member 14, which is placed in cartridge 152, and the cartridge walls 154 is limited, but allows for the positioning member 14 to be readily disposed within the cartridge 152 (FIG. 14). Additionally, the cartridge walls 152 are spaced to correspond to the dimensions of the lower recessed chamber 138. As illustrated in FIG. 13, the cartridge walls 154 are preferably spaced such that the cartridge 152 is slightly wider and longer than lower wall portions 142 of the lower recessed chamber 138. In this manner, the lower wall portions 142 are insertable within the cartridge 152. Cartridge 152 may also include flanges 156 that extend outwardly from walls 154. Flanges 156 allow a surface for grasping or handling the cartridge 152 and aid the user in engaging or disengaging the cartridge 152 into the snap-fit connection 140.

When the cartridge 152 is connected to the base mold 112 through the snap-fit connection 140, a received positioning member 14 is generally captured or secured within the base mold 112. For example, as illustrated in the enlarged cross-sectional view of FIG. 14, a received positioning member 14 is preferably pinched between at least one bottom edge 144 and the cartridge bottom wall 130. In this manner, a peripheral edge portion 153 of the received positioning member 14 is secured within the base mold 112 when the cartridge 152 is connected to the lower recessed chamber 138.

As illustrated in FIGS. 13 and 14, the snap-fit arrangement 140 generally includes a elongated boss or protrusion 158 and a corresponding elongated recess 160. Preferably, the protrusion 158 is in the lower wall portion 142 and the recess 160 is in the cartridge wall 154; however, other arrangements are possible, such as the opposite configuration of the protrusion 158 in the cartridge wall 154 and the recess 160 in the lower wall portion 142. Moreover, one skilled in the art will appreciate that the protrusion 158 and recess 160 may have various shapes and sizes so long as the snap-fit connection secures cartridge 152 to the lower recessed chamber 138.

To provide the snap-fit arrangement 140, the protrusion 158 seats in the recess 160. In this manner, the seated protrusion 158 secures the cartridge 152 to the lower recessed chamber 138. More specifically, the lower wall portion 142 preferably has an angled leading surface 162, which guides the lower recessed chamber 138 into the cartridge 152. Likewise, cartridge walls 154 also preferably include an angled leading surface 164 to further guide the chamber 138 into cartridge 152. To seat the protrusion 158, cartridge wall 154 preferably has at least one cam surface 166 that pivots either the cartridge wall 154 or the lower wall portion 142 outwardly so that the protrusion 158 may traverse past the leading surface 164 and cam section 166 into the recess 160. Once seated, the cartridge wall 154 or the lower wall portion 142 pivots back into its original orientation.

In accordance with the method of the present invention, a tissue sample is processed for evaluation, as illustrated in FIG. 15. The tissue sample 15 first is collected 70 and is deposited 72 on the mounting card 14. The tissue sample 15 is positioned on the mounting card 14 preferably immediately after being collected if the entire sample is to be examined, or once the pathologist or surgeon has selected a particular aliquot from the tissue sample, so that the orientation of the selected plane is preserved throughout processing. Preferably, the tissue sample 15 is deposited with the selected plane disposed downwardly in contact with the top layer 20 of the mounting card 14. By thus positioning the tissue sample 15, the selected plane will be located at the outer face of the wax block after the casting step so that, when the block is sectioned using the microtome, the selected plane will be in the leading sections cut from the block.

With a fresh tissue sample, the tissue sample 15 is generally removably mounted on the mounting card 14 as a result of the protein bridge formed with the second layer 22. If desired, a fixative, such as a protein glue, may be applied 71 to the outer surface of the top layer 20 prior to mounting of the sample on the card 72 to further adhere the tissue sample 15. Suitable glues, which are compatible with the specimen and which do not interfere with contact of the various processing fluids, include proteinaceous adhesives and polysaccharide adhesives. Suitable proteinaceous adhesives include gelatin and casein. Suitable polysaccharide adhesives include agar, arabinose, carrageenan, and pectin. In general, it is preferred to use proteinaceous adhesives for fresh, non-fixed tissue specimens and to use polysaccharide adhesives for previously fixed tissue samples. Additionally, a jellied fixative may be deposited 74 over the tissue sample 15 which has been positioned on the mounting card 14 to further preserve the integrity of and adhere the tissue sample 15. Suitable jellied fixatives include carbopol or equivalent 0.5% to 1.0% fixative, such as alcohol, formaldehyde, glyoxal, water or 10% solution of formalin.

With the tissue sample 15 mounted on the card 14, the mounting card 14 is deposited 76 within the cassette 11. A lid 13 encloses the mounting card 14 within the cassette. The cassette 11 with mounting card 14 is deposited in a bag or otherwise packaged in a suitable manner for transport, as needed.

As shown by process path A, the tissue sample 15 is next subjected to tissue processing 78. Solvent processing 78 of the tissue sample 15 may be completed using equipment and techniques known to one of ordinary skill in the art. The mounting card 14 remains enclosed in the cassette during the processing period and is subjected to a flow of tissue treating fluids. During processing 78, the tissue sample 15 is contacted with the desired solvents for dehydrating and clearing the sample.

After processing 78 is completed, the mounting card 14 is removed from the cassette 11. The mounting card 14 is next deposited 80 in the base mold 12, 112, or 112a in the lower chamber 38 in preparation for casting in wax. The cassette 11 is disposed 82 in the receiving area 48 of the base mold 12 above the mounting card 14. When using the base mold 12 of the first embodiment of the present invention, the tissue sample 15 and mounting card 14 are ready for wax casting. Alternatively, a vacuum 84 may be drawn on the base mold 12 prior to and/or during the wax casting step (FIG. 13).

Instead of process path A, process path B can alternatively be used where the tissue sample 15 instead is processed in-line within the base mold 12 (FIG. 14). After the tissue sample 15 has been collected, mounted and transported, the mounting card 14 with tissue sample 15 is removed from the cassette 11 and deposited 86 in the base mold 12, 112, or 112a in the lower chamber 38. The cassette 11 is disposed 88 in the receiving area 48 of the base mold 12 above the mounting card 14. The base mold 12 is connected to a solvent process line 64, as described above in one of the alternative embodiments, and tissue processing 90 is commenced. When processing 90 is completed, the process line 64 is disconnected, and a vacuum line 62 may be connected, if it is desired to draw a vacuum 92.

Next, with all embodiments of the base mold 12, molten embedding material is introduced 94 through the apertures in the bottom wall 17 of the cassette 11 and into the base mold 12. Liquified embedding material is poured into the mold and around the tissue sample 15 on the mounting card 14, filling the interior regions of the base mold 14 and the cassette 11, and cooled 96, thereby casting the tissue sample 15 in a block.

When the tissue sample 15 and cassette 11 are embedded in the block of solidified paraffin wax, the block is removed 98 from the base mold 12 as previously described. As the block is removed from the base mold 12, the block with tissue sample 15 embedded therein is separated from the mounting card 14, which preferably remains in the base mold 12. The cassette 11 serves as the base of the block opposite the outward, selected face of the tissue sample 15. The sample is then processed per standard procedures with a microtome.

Numerous modifications to the invention are possible to further improve the processing of a tissue sample for histological examination. Thus, modifications and variations in practice of the invention will be apparent are expected to those skilled in the art upon consideration of the foregoing detailed description of the invention. Although preferred embodiments have been described above and illustrated in the accompanying drawings, there is no intent to limit the scope of the invention to these or other particular embodiments.

What is claimed is:

1. A system for use in processing a tissue specimen for histological examination comprising: a tissue specimen positioning member of a material that removably maintains the tissue specimen in a predetermined position thereon for providing the specimen with a known, consistent orientation throughout processing; a carrier member for receiving the positioning member with tissue specimen thereon and for subsequently mounting in a microtome the tissue specimen as processed to be associated with a fixing medium; and a base member having a lower recessed chamber sized to receive the tissue specimen positioning member with tissue specimen thereon and to maintain the positioning member therein upon application of a separation force between the positioning member and the tissue specimen for removing the tissue specimen from the base member.

2. The system in accordance with claim 1, wherein the positioning member includes a first material for holding the tissue specimen in a generally fixed orientation when the tissue specimen is deposited on the positioning member and a second material for allowing separation of the tissue specimen from the positioning member upon application of a separation force.

3. The system in accordance with claim 2, wherein the base member has a front wall and a back wall each having lines of weakness for facilitating breaking away of the walls from the base member upon application of a separation force to the walls to allow access into the interior of the base member for removal of the tissue sample from the positioning member contained therein.

4. The system in accordance with claim 3, wherein the base member has an opening in the lower chamber sized for connection of a process line with the base member for introduction into and removal from the base member of fluids and air through the process line.

5. The system in accordance with claim 1, wherein the lower recessed chamber comprises a removable bottom wall, a plurality of side walls having bottom edges, and a snap-fit connection between the bottom wall and at least one of the side walls.

6. The system in accordance with claim 5, wherein the removable bottom wall defines a cartridge sized for receiving the positioning member such that a peripheral edge portion of a received positioning member is securable between a connected bottom wall and the bottom edge of at least one lower recessed chamber side wall.

7. The system in accordance with claim 6, wherein the snap-fit connection comprises a protrusion on at least one lower recessed chamber side wall and a corresponding recess in the cartridge such that the protrusion is engageable within the recess to secure the removable bottom wall to the lower recessed chamber.

8. The system in accordance with claim 6, wherein the snap-fit arrangement comprises a recess in at least one lower recessed chamber side wall and a corresponding protrusion on the chamber such that the protrusion is engageable within the recess to secure the removable bottom wall to the lower recessed chamber.

* * * * *